US009511002B2

(12) United States Patent
Chaturvedi et al.

(10) Patent No.: US 9,511,002 B2
(45) Date of Patent: Dec. 6, 2016

(54) SENSOR EQUIPPED MEDICINAL CONTAINER

(71) Applicant: Nant Holdings IP, LLC, Culver City, CA (US)

(72) Inventors: Rahul Chaturvedi, San Diego, CA (US); Patrick Soon-Shiong, Los Angeles, CA (US); Emerico Alberto Brewer, Chula Vista, CA (US); Jin Hyup Lee, San Diego, CA (US)

(73) Assignee: NANT HOLDINGS IP, LLC, Culver City, CA (US)

( * ) Notice: Subject to any disclaimer, the term of this patent is extended or adjusted under 35 U.S.C. 154(b) by 0 days.

(21) Appl. No.: 15/014,796

(22) Filed: Feb. 3, 2016

(65) Prior Publication Data
US 2016/0151247 A1    Jun. 2, 2016

Related U.S. Application Data

(63) Continuation of application No. 14/350,054, filed as application No. PCT/US2012/059203 on Oct. 8, 2012, now Pat. No. 9,308,151.
(Continued)

(51) Int. Cl.
G08B 21/00 (2006.01)
A61J 7/04 (2006.01)
(Continued)

(52) U.S. Cl.
CPC .. *A61J 7/04* (2013.01); *A61J 1/03* (2013.01); *A61J 1/10* (2013.01); *A61J 1/1412* (2013.01); *A61J 1/18* (2013.01); *A61J 7/02* (2013.01); *G06F 19/3456* (2013.01); *A61B 2050/314* (2016.02); *A61J 7/0418* (2015.05); *A61J 7/0436* (2015.05); *A61J 2200/30* (2013.01); *A61J 2205/20* (2013.01); *A61J 2205/60* (2013.01); *A61J 2205/70* (2013.01); *G06F 19/3462* (2013.01)

(58) Field of Classification Search
CPC .................. A61J 1/10; A61J 1/03; A61J 1/16; A61J 7/04; G06F 1/00
USPC ...................... 340/540, 539.12, 547, 309.16, 407.1,340/815.4, 384.1; 221/10
See application file for complete search history.

(56) References Cited

U.S. PATENT DOCUMENTS 5,170,380 A    12/1992 Howard et al.
5,421,981 A    6/1995 Leader et al.
(Continued)

FOREIGN PATENT DOCUMENTS

WO    WO 2009/051476    4/2009

OTHER PUBLICATIONS

PCT International Search Report and Written Opinion in PCT International Application Serial No. PCT/US2012/059203, mailed on Dec. 11, 2012 (8 pages).
(Continued)

*Primary Examiner* — Phung Nguyen
(74) *Attorney, Agent, or Firm* — Stetina Brunda Garred & Brucker

(57) ABSTRACT

Medicinal container bags are presented. Bags can include openers capable of sealing an opening of the bag. Disclosed bags further comprise electronic assemblies configured to detect opening or closing events as the openers move along the rims of the bag opening. The assemblies can compile usage data based on opener movement, and then provide the data to remote monitoring systems.

20 Claims, 9 Drawing Sheets

Related U.S. Application Data

(60) Provisional application No. 61/543,945, filed on Oct. 6, 2011.

(51) Int. Cl.
*G06F 19/00* (2011.01)
*A61J 1/10* (2006.01)
*A61J 1/14* (2006.01)
*A61J 1/18* (2006.01)
*A61J 7/02* (2006.01)
*A61J 1/03* (2006.01)

(56) References Cited

U.S. PATENT DOCUMENTS

| | | | |
|---|---|---|---|
| 6,070,628 A | 6/2000 | Nastasi | |
| 6,361,642 B1 * | 3/2002 | Bellamy | A61J 1/05 |
| | | | 156/245 |
| 6,529,446 B1 | 3/2003 | de la Huerga | |
| 7,198,172 B2 | 4/2007 | Harvey et al. | |
| 7,269,476 B2 | 9/2007 | Ratnakar | |
| 7,276,675 B2 | 10/2007 | Faries, Jr. et al. | |
| 7,295,890 B2 | 11/2007 | Jean-Pierre | |
| 7,350,669 B2 * | 4/2008 | Rani | A61J 1/10 |
| | | | 215/249 |
| 7,406,259 B1 * | 7/2008 | Wilhelm | G03B 7/26 |
| | | | 396/301 |
| 7,407,796 B2 | 8/2008 | Hammerstedt et al. | |
| 7,424,888 B2 | 9/2008 | Harvey et al. | |
| 7,715,277 B2 | 5/2010 | de la Huerga | |
| 7,801,745 B2 | 9/2010 | Walker et al. | |
| 7,844,361 B2 | 11/2010 | Jean-Pierre | |
| 7,978,564 B2 | 7/2011 | de la Huerga | |
| 8,378,812 B2 * | 2/2013 | Choi | A61J 7/0409 |
| | | | 340/539.11 |
| 8,391,104 B2 * | 3/2013 | de la Huerga | A61J 1/035 |
| | | | 206/459.5 |
| 2002/0104848 A1 | 8/2002 | Burrows | |
| 2003/0048187 A1 * | 3/2003 | Nolte | A61J 1/1462 |
| | | | 340/572.8 |
| 2007/0016443 A1 | 1/2007 | Wachman et al. | |
| 2007/0024465 A1 | 2/2007 | Howell et al. | |
| 2007/0073560 A1 | 3/2007 | Walker et al. | |
| 2008/0136629 A1 | 6/2008 | Mahoney | |
| 2008/0162192 A1 | 7/2008 | Vonk et al. | |
| 2009/0043605 A1 | 2/2009 | Imai et al. | |
| 2009/0128330 A1 | 5/2009 | Monroe | |
| 2009/0134181 A1 | 5/2009 | Wachman et al. | |
| 2009/0195400 A1 * | 8/2009 | Oreshkin | A41D 1/002 |
| | | | 340/686.1 |
| 2009/0294521 A1 | 12/2009 | de la Huerga | |
| 2010/0102930 A1 | 4/2010 | McCoy | |
| 2010/0270257 A1 | 10/2010 | Wachman et al. | |
| 2010/0328099 A1 | 12/2010 | Wachman et al. | |
| 2015/0027918 A1 | 1/2015 | Chaturvedi et al. | |

OTHER PUBLICATIONS

PCT International Preliminary Report on Patentability in PCT International Application Serial No. PCT/US2012/059203, mailed on Apr. 8, 2014.

\* cited by examiner

SENSOR EQUIPPED MEDICINAL CONTAINER

This Application is a continuation of, and claims the benefit of priority under 35 U.S.C. §120, of U.S. patent application Ser. No. 14/350,054 filed on Apr. 4, 2014, now issued as U.S. Pat. No. 9,308,151, and entitled SENSOR EQUIPPED MEDICINAL CONTAINER, which application is a national stage application under 35 U.S.C. 371 of U.S. International Application No. PCT/US2012/059203 filed on Oct. 8, 2012 and entitled SENSOR EQUIPPED MEDICINAL CONTAINER, which application claims the benefit of priority to U.S. Provisional Patent Application Ser. No. 61/543,945 filed on Oct. 6, 2011 and entitled SENSOR EQUIPPED MEDICINAL CONTAINER. The disclosures of the prior Applications are considered part of and are hereby incorporated by reference in their entirety in the disclosure of this Application.

FIELD OF THE INVENTION

The field of the invention is medical container technologies.

BACKGROUND

Ensuring a patient follows a medication or dosage regime continues to be problematic in the medical industry. Previous efforts directed toward compliance focused on incorporating reminders into various medicinal containers. For example, U.S. patent application publication 2007/0016443 to Wachman et al. titled "Medication Compliance Systems, Methods and Devices with Configurable and Adaptable Escalation Engine", filed Jul. 6, 2006, describes incorporating electronics into a container cap where the electronics can provide compliance feedback to a patient or to remote healthcare providers. Interestingly, the disclosed effort and other known efforts focus on specific containers; bottles, vials, boxes, or blister packs for example, rather than a single container, a bag for example, suitable for all types of pharmaceuticals. Further, the known art fails to address issues that arise from bag-like containers having flexible seals, which render detection of an open or close event very difficult.

U.S. patent application publication 2002/00104848 to Burrows et al. titled "Pharmaceutical Container Having Signaling Means and Associated Method of Use", filed Feb. 5, 2001, describes a use of a sensor to determine the closed position of a cap. Contemplated containers transmit data with a base station. Although Burrows presents useful approaches for tracking a patient's compliance with a schedule, Burrows requires container-specific implementations for each type of medicine container. In the Burrows example, the disclosed technique is only applicable to rigid container openings.

U.S. patent application publication 2007/0024465 to Howell et al. titled "Portable Container with Speaker Attached", filed Jul. 22, 2006, describes a bottle having a speaker capable of providing audio signals to remind patients to take substances in the bottle. Howell references that some embodiments include storing a bottle in a bag, but fails to address issues relating detecting when a flexible seal of the bag is opened or closed.

Yet another example includes U.S. patent application publication 2009/0294521 to de la Huerga titled "Interactive Medication Container", filed May 8, 2009. The de la Huerga disclosure describes interactive medication containers that inform a patient or pharmacist about compliance with dosage requirements. Even though de le Huerga contemplates interactive systems for bottles, boxes, or blister packs, de la Huerga also fails to address problems arising from a bag-like container having a flexible opening. The disclosed de la Huerga containers also comprise rigid caps or containers.

Additional examples include U.S. Pat. Nos. 7,295,890 and 7,844,361 both to Jean-Peirre and titled "Prescription Drug Compliance Monitoring System", filed Sep. 25, 2003 and Oct. 30, 2007, respectively. In the Jean-Pierre approach medical dispensers alert patients take medication and gathers compliance data. The dispensers also have rigid openings.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Thus, there is still a need for bag containers having non-rigid openings capable of providing schedule or compliance feedback.

SUMMARY OF THE INVENTION

The inventive subject matter provides apparatus, systems and methods in which a bag can include one or more sensors to detect an opening or a closing of a flexible or non-rigid seal. One aspect of the inventive subject matter includes a sensor equipped bag having a main body that includes a cavity defined by flexible walls. The main body also comprises an opening providing access to the cavity. The main body further comprises a flexible seal assembly attached to a rim portion of the opening where the seal assembly is configured to seal the cavity. Example seal assemblies can include magnets, zip-locks, zippers, draw strings, or other seals. The bags can also include an opener coupled with the seal assembly that opens and closes the mechanical seal upon actuation of the opener by mechanically coupling or decoupling the non-rigid rims of the opening. An electronic assembly, possibly disposed in the bag or in the opener, includes circuitry capable of detecting an opening or closing event when the opener is actuated based on proximity of the opener to an opener sensor. In more preferred embodiments, the opener includes a magnet, or other passive trigger, and the electronic assembly utilizes a Hall Effect sensor to detect proximity of the magnet. Thus, the bag can determine if the bag has been opened or closed indicate possible access to the contents of the bag.

Various objects, features, aspects and advantages of the inventive subject matter will become more apparent from the following detailed description of preferred embodiments, along with the accompanying drawing figures in which like numerals represent like components.

DETAILED DESCRIPTION

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including providing for detecting of opening or closing events of a non-rigid medical container opening.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of a networking environment the terms "coupled to" and "coupled with" are used euphemistically to mean "communicatively coupled with" where two or more networked elements are configured to exchange data over a network, possibly via one or more intermediary devices.

Figure 1A:
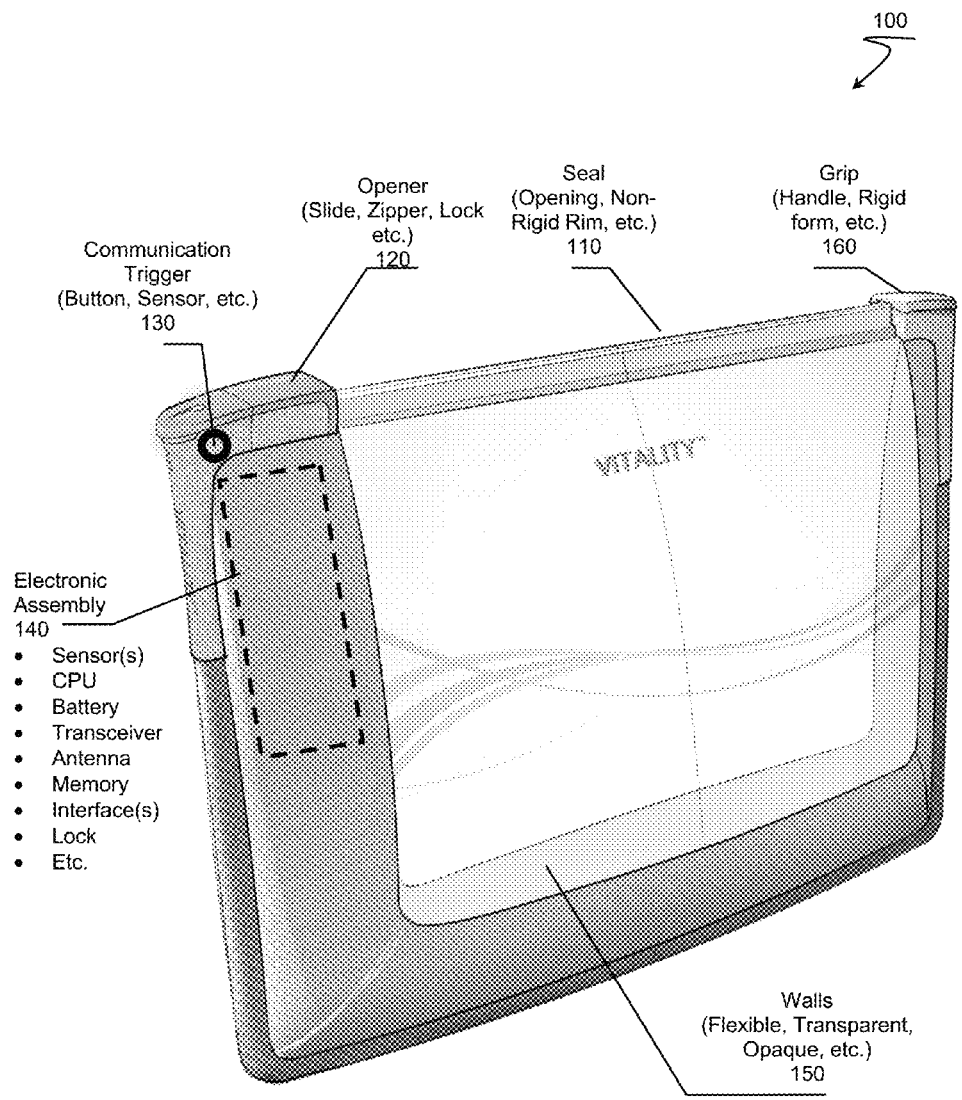
FIG. 1A is a schematic of a medicinal container bag capable of sensing when a flexible seal on the bag is opened or closed.

FIG. 1A illustrates one possible embodiment of a contemplated bag 100, preferably a medicinal container. Bag 100 can be used to store various types of pharmaceuticals including pills, blister packs, injectables, liquid doses, vials, surgical tools, bandages, bottles, syringes, or other types of medicine or dispensers. Bag 100 includes a main body having a cavity defined by flexible walls 150. Flexible walls 150 allow the bag to accommodate a wide variety of the possible contents.

Contemplated bags 100 also include a flexible seal assembly represented by seal 110 disposed around a rim portion of the cavity opening. In the example shown, seal 110 comprises non-rigid rims capable of forming a zip lock seal. Seal 110 allows the bag to flex, bend, or move even when the bag is sealed. Example the non-rigid rims can include zip-locks (e.g., tongue and groove, interlocking ribs or ridges, etc.), zippers, draw strings, magnets, or other types of seal assemblies. Seal 110 is configured to resist or restrict opening without use of a seal opener 120. Seals 110 that restrict access to the contents are considered advantageous to allow electronic circuitry represented in as electronic assembly 140 in the bag to log or track actual opening or closing events as discussed later.

Bag 100 can also include opener 120 coupled with seal 110 where opener is capable of opening or closing the seal assembly by coupling or decoupling the non-rigid rims. Thus, opener 120 can shift or slide from one side of bag 100 to open bag 100 by separating the non-rigid rims, or shift or slide from the other side of bag 100 to close bag 100 by joining the non-rigid rims.

Opener 120 can be complementary to the type of seal 110 employed on bag 100. As illustrated opener 120 is configured to open or close a tongue-groove seal assembly similar to those employed in zip-lock bags. In other embodiments, opener 120 can include a zipper, draw strings, magnets, or other types of openers.

In some embodiments, opener 120 can include a sensor or a sensor trigger that can be used to determine if opener 120 is in an open or closed position, or other position between a completely opened or closed position. Opener 120 can include slots allowing portions of the seal assembly's non-rigid rims to slide through opener 120. Thus opener 120 can accommodate a flexible seal 110 while also providing an indication that the contents of bag 100 have been accessed.

Tracking an open or close state of bag 100 provides useful information related to ensuring a patient complies with a medicinal regimen. When bag 100 is open, the opening event can be considered to indicative of a use of the contents. Further, the duration of time between the opening event and the closing event can be indicative of a use time. One should appreciate that the non-rigid rims and opener 120 can be configured to detect when bag 100 is partially opened. For example, the non-rigid rims could include resistive stripes. As opener 120 moves along the rims a sensor can measure an electrical resistance between a closed position of opener 120 and a current position of opener 120 where electrical resistance indicates how far opener 120 has moved. Such information can be used to indicate if a specific content has been removed. A large blister pack might require a large opening. Thus, when opener 120 is in position that is sufficient to allow removal of the large blister pack, then the opening event can be considered, at least to some extent, a valid use of the blister pack.

Figure 4:
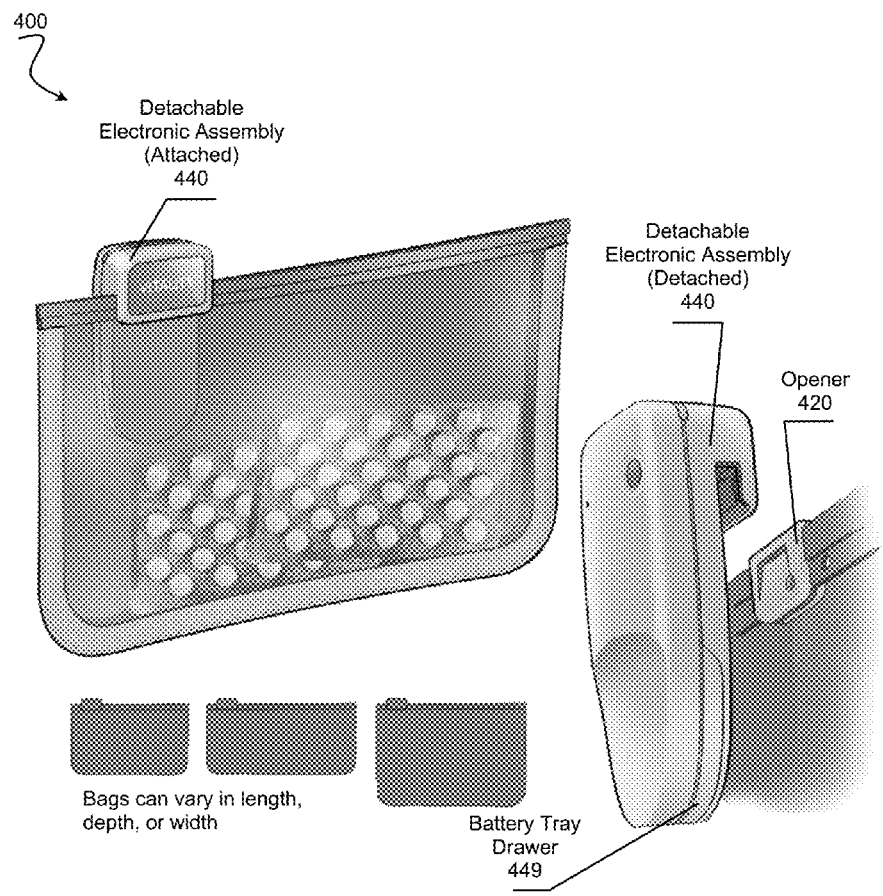
FIG. 4 illustrates a possible alternative embodiment of an inventive bag.

Bag 100 can also incorporate electronic assembly 140 having an opener sensor circuit that is configured to detect proximity of opener 120 to an opener sensor. Electronic assembly 140 can be disposed in the bag as illustrated by the dashed line or disposed in or about opener 120 as illustrated in FIG. 4 discussed below. Electronic assembly 140 can further include sensors, processors (e.g., microcontroller, CPU, ASIC, FPGA, etc.), memory (e.g., RAM, ROM, Flash, solid state drive, etc.), batteries, transceivers, antenna, memory, locks, or other types of components.

Some embodiments also comprise communication activation trigger 130, possibly a button, coupled with electronic assembly 140. Upon actuation of communication activation trigger 130, electronic assembly 140 can construct a message and send the message to a remote computing device (e.g., communication hub, router, remote server, etc.). Consider a bag storing doses of a prescription. Based on the number of opening or closing events detected due to motion of opener 120, electronic assembly 140 can track at least can estimated number of doses used. If the estimated number of doses, or other information, satisfies refill criteria, then communication activation trigger 130 can provide an indication that a refill is due. Alternatively, a patient can actuate communication activation trigger 130 to send a refill message to a pharmacy, or send other possible messages to remote entities. Refill techniques disclosed in U.S. patent application publication 2010/0270257 to Wachman et al. titled "Medicine Bottle Cap with Electronic Embedded Curved Display", filed Apr. 29, 2010, can be adapted for use with the inventive subject matter disclosed herein.

Figure 1B:
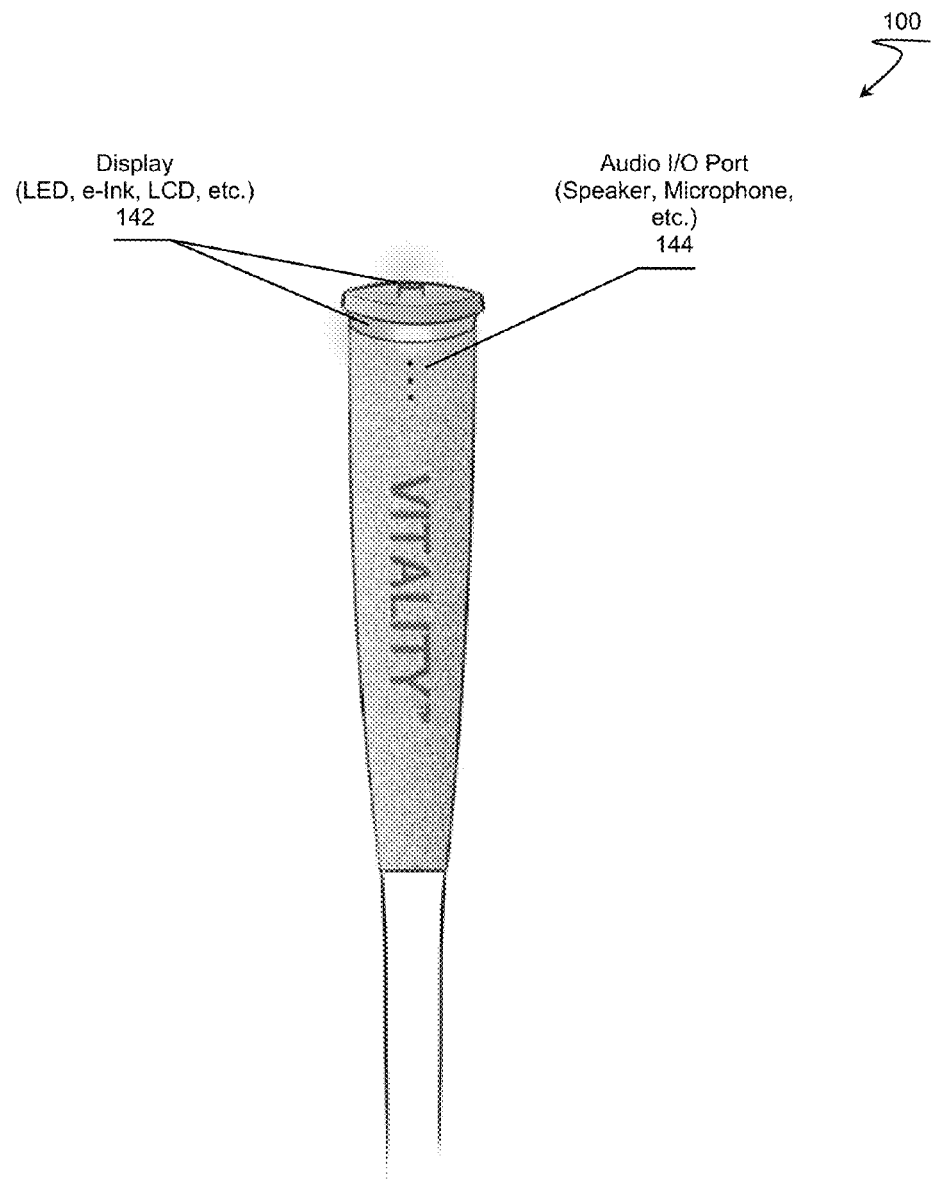
FIG. 1B a front view of the bag from FIG. 1A illustrating a display and an audio I/O port.

FIG. 1B provides a more detailed view of a spine or edge of bag 100 illustrating possible indictors that can be incorporated into bag 100. Electronic assembly 140 can provide feedback to a patient or consumer via the indicators. In the example shown, bag 100 includes display 142 and audio I/O port 144. Display 142 is shown as two LEDs ports allowing color coded light to be emitted to present compliance information to a user. Of particular note, the LEDs are positioned on top of the spine and on a forward-facing portion of the spine. Such an approach is considered advantageous because the LEDs can be observed when bag 100 is positioned in different orientations relative to a user, possibly where multiple bags 100 are stacked on top of each other or placed in a shelf in a vertical position. Audio I/O port 144 can comprises a speaker capable of providing auditory information to the consumer. Further, audio I/O port 144 can include a microphone in embodiments supporting bi-directional voice communications (e.g., VoIP, SIP, H.323, etc.). Other types of indicators can include a tactile display capable of generating textures (e.g., Braille, etc.), e-ink displays, LCD displays, LED displays as shown, or other types of indicators.

The indicators illustrated in FIG. 1B are positioned on a corner of the bag along one spine or edge. Still, the displays could be placed at other locations about the bag. For example, an e-ink display or other flexible display can be positioned on an external surface of the bag where it can be read by the consumer possibly on walls 150.

Figure 1C:
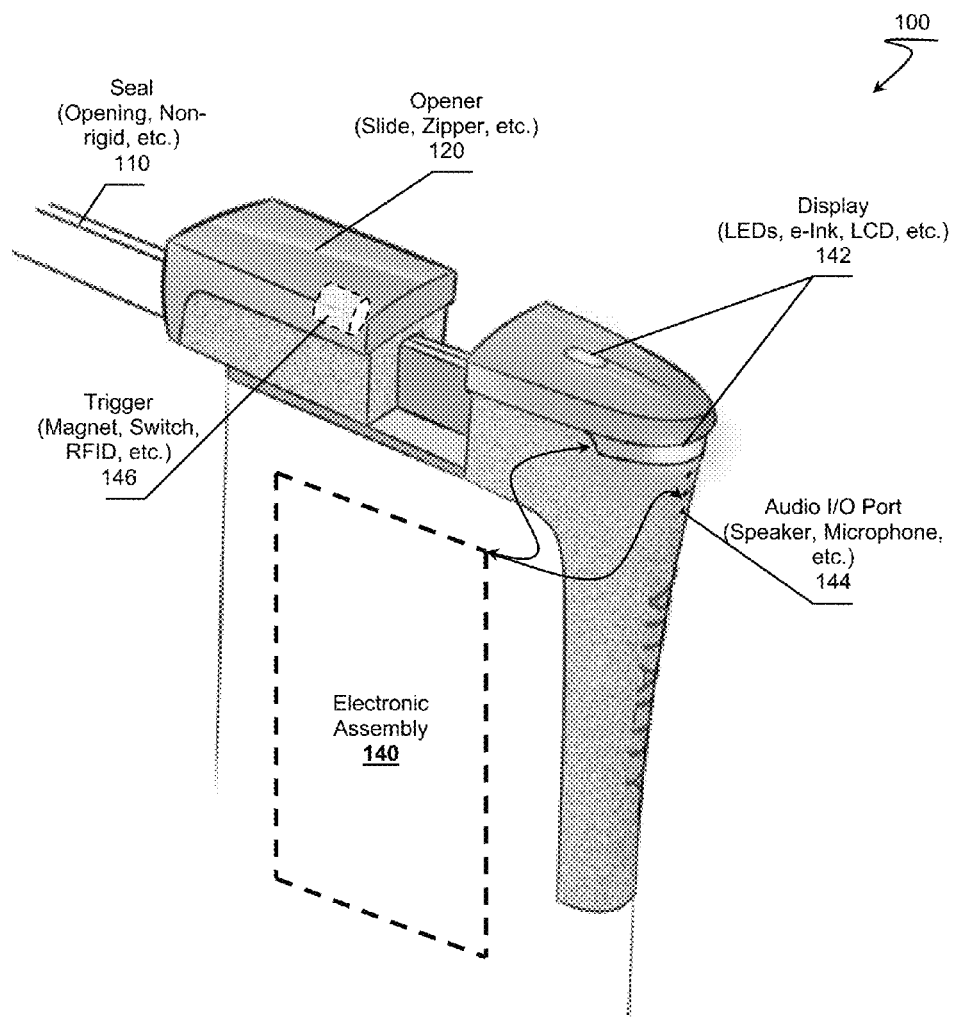
FIG. 1C provides a view where an opener of the bag from FIG. 1A is moved to partially open the bag.

FIG. 1C provides a more detailed view of bag 100 and operation of opener 120. In this example, opener 120 includes trigger 146, a magnet for example, which can be used to trigger a complementary opener sensor monitored by electronic assembly 140. Electronic assembly 140 can comprise opener sensor, or an interface to the opener sensor, which detects opening or closing events upon actuation of opener 120 along the non-rigid rims based on proximity opener 120 to the sensor. For example, the sensor can remain stationary with respect to walls 150 and as opener 120 moves away from the sensor, the senor can detect the position of opener 120. One aspect of an opener sensor can include a Hall Effect sensor to detect proximity of the magnet in the opener 120. Other types of triggers can include passive triggers (e.g., magnets, RFID chips, etc.) or active triggers. Example active triggers can include mechanical (e.g., mechanical switch on a zipper, etc.) or electrical components that actively engage with electronic assembly 140 to track opener actuation events.

Opener actuation events include a broad spectrum of information relating to opener 120. In a basic form, electronic assembly 140 can simply detect when opener 120 shifts between a closed position, possibly based on proximity relative to an opener sensor, and a closed position. In more complex embodiments, electronic assembly 140 can track many other attributes or properties of opener actuation events. Opener attributes can include opener position relative to an edge of the bag, force or grip pressure applied to the opener, rate at which the opener is moved, duration of use, relative position to closed position, or other sensed data. The sensed or measured opener attributes provide information indicative of how a consumer or patient interacts with bag 100. For example, an elderly person might have difficulty gripping opener 120, thus might require further assistance as indicated by a piezoelectric sensor. Such data can be transmitted to remote or external computing devices for further analysis via a transceiver coupled with electronic assembly 140.

Bag 100 can also include a lock, possibly disposed within opener 120 or electronic assembly 140, which locks opener 120 into a closed position. When scheduling criteria is met, electronics assembly 140 can unlock opener 120 to allow access to the contents stored within the bag 100. The lock could include a mechanical lock that physical holds opener 120 in a closed position. Alternatively, the lock could include a magnetic lock that electro-magnetically keeps opener 120 in a closed position. In such an embodiment, electronic assembly 140 can disengage the magnetic lock as necessary.

Figure 1D:
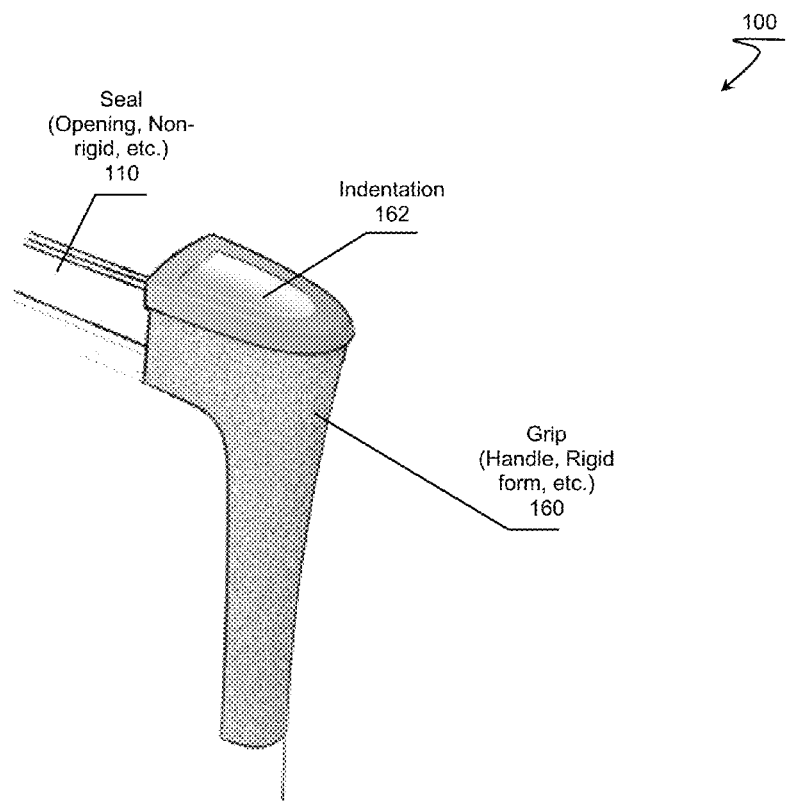
FIG. 1D provides a detailed view of a grip or handle for the bag from FIG. 1A.

As illustrated in FIG. 1D, bag 100 can include one or more bag identifiers (e.g., user name, symbol, logo, owner name, prescription number, GUID, UUID, MAC address, network address, etc.), which can be used to differentiate one bag from another. In the example shown, a bag identifier can be inserted into indentation 162 of grip 160 associated with bag 100. For example, a marker or other item can be sized or dimensions to insert into identification 162. The marker preferably includes symbols or colors that distinguish bag 100 from other bags, or that allow for identification by individuals suffering from colorblindness or blurred vision. Further, the markers can communicatively couple with electronic assembly 140 (e.g., RFID tag, memory, etc.) to allow electronic assembly 140 to obtain an identifier from the marker, thus allowing electronic assembly 140 to notify remote computing devices (e.g., base stations, servers, services, cell phones, etc) of the bag's identification. The markers can be permanently attached or can be removeably attached to the bag possibly through chemical, mechanical, or magnetic techniques.

Figure 1E:
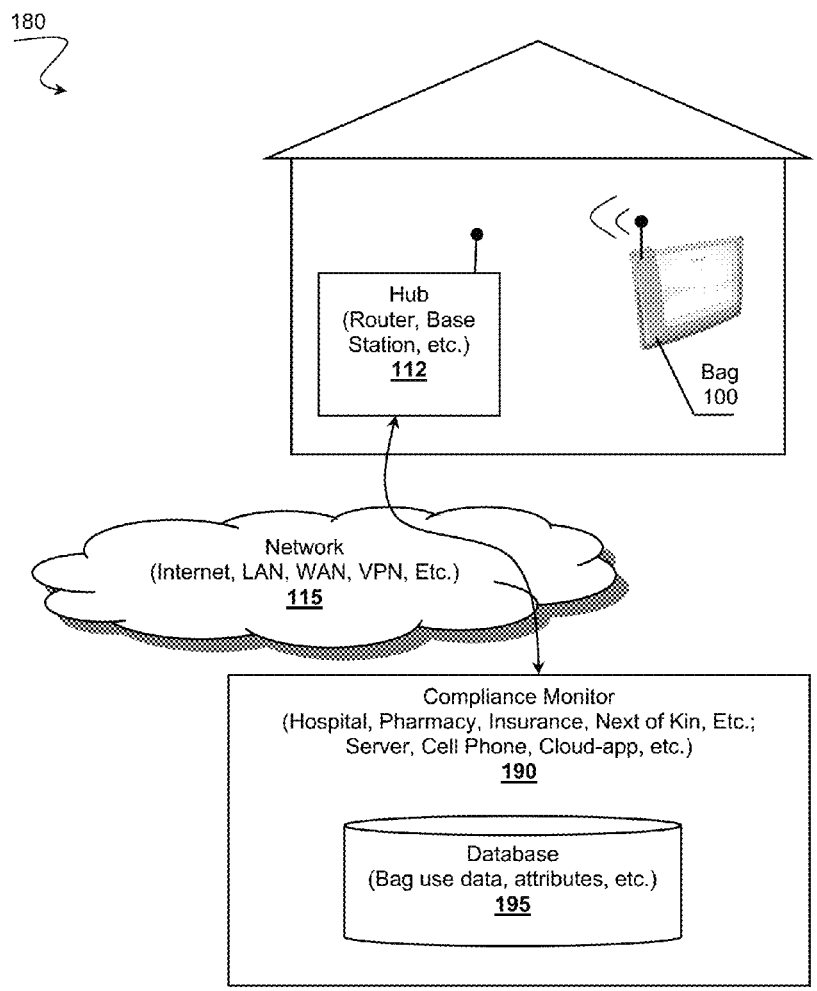
FIG. 1E illustrates a compliance ecosystem in which the bag from FIG. 1A can exist.

In some embodiment, bag 100 can integrate into monitoring, compliance, or scheduling ecosystem 180 as illustrated in FIG. 1E. Electronic assembly 140 of bag 100 can include a transceiver and antenna through which it can exchange medical or other type of compliance or scheduling data with compliance monitor 190. The example illustrates bag 100 wirelessly exchanges data with hub 112, which in turn exchanges data over network 115 (e.g., the Internet, WAN, LAN, VPN, cellular, etc.) with compliance monitor 190. Example wireless protocols suitable for use with bag 100 include 802.11, WiMAX, Bluetooth, Zigbee, cellular, RF, IrDA, or other wireless protocols.

Hub 112 can be considered an optional element in ecosystem 180. For example, bag 100 could include a cellular radio capable of establishing a connection with compliance monitor 190 over a cellular network 115. It is contemplated that most market-relevant implementations will include hub 112, which would likely be substantially local to the locale where bag 100 will be used. In such cases, hub 112 could include a wireless router, a dedicated communication hub, a game console, a set top box, a tablet or cell phone, or other suitably adapted computing device.

Compliance monitor 190 can also take on different forms. In some embodiments, compliance monitor 190 can include a for-fee service providing access to servers capable of aggregating data from bag 100 in database 195. Based on notification criteria, monitor 190 can contact other third party entities as desired, or even establish communications with bag 100. For example, compliance monitor 190 could establish a VoIP session with user via bag 100.

Figure 2A:
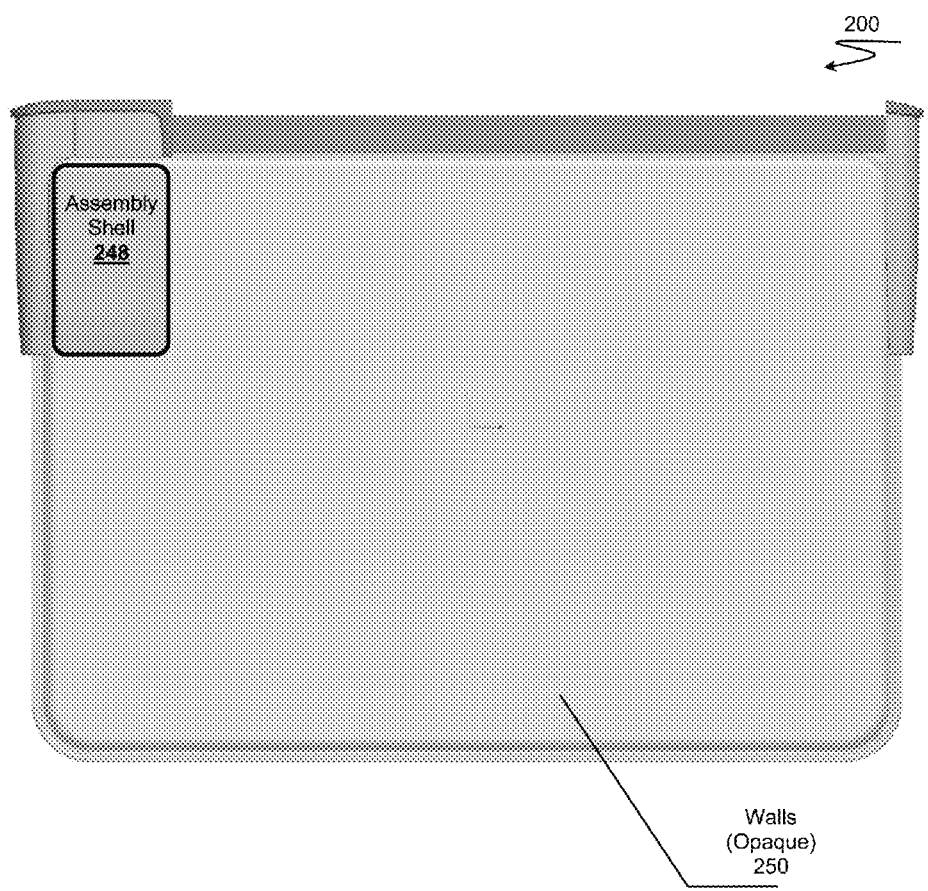
FIG. 2A illustrates an embodiment of a medicinal container bag with opaque walls.
Figure 2B:
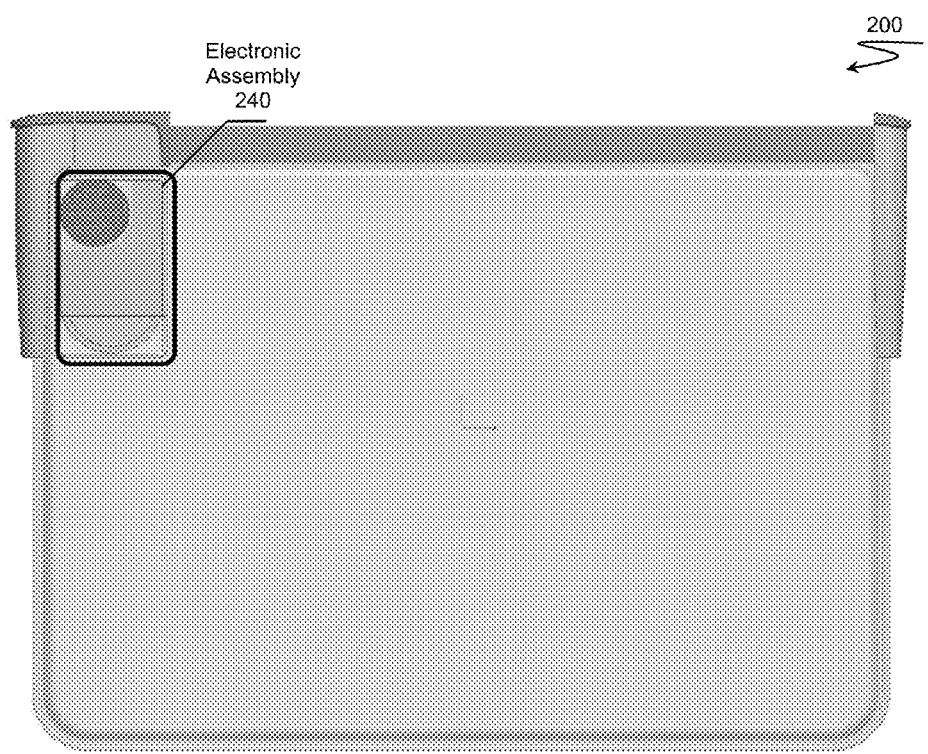
FIG. 2B reveals placement of an electronic assembly of the bag from FIG. 2A.

FIGS. 2A and 2B illustrate another embodiment of bag 200 where the electronic assembly 140 is disposed within shell 248 on the inside of the bag. In FIG. 2B the electronic assembly is revealed from beneath the shell. Further, bag 200 comprises opaque walls 250. Opaque walls 250 can be advantageous in circumstances where medicinal contents would be light sensitive.

Figure 3:
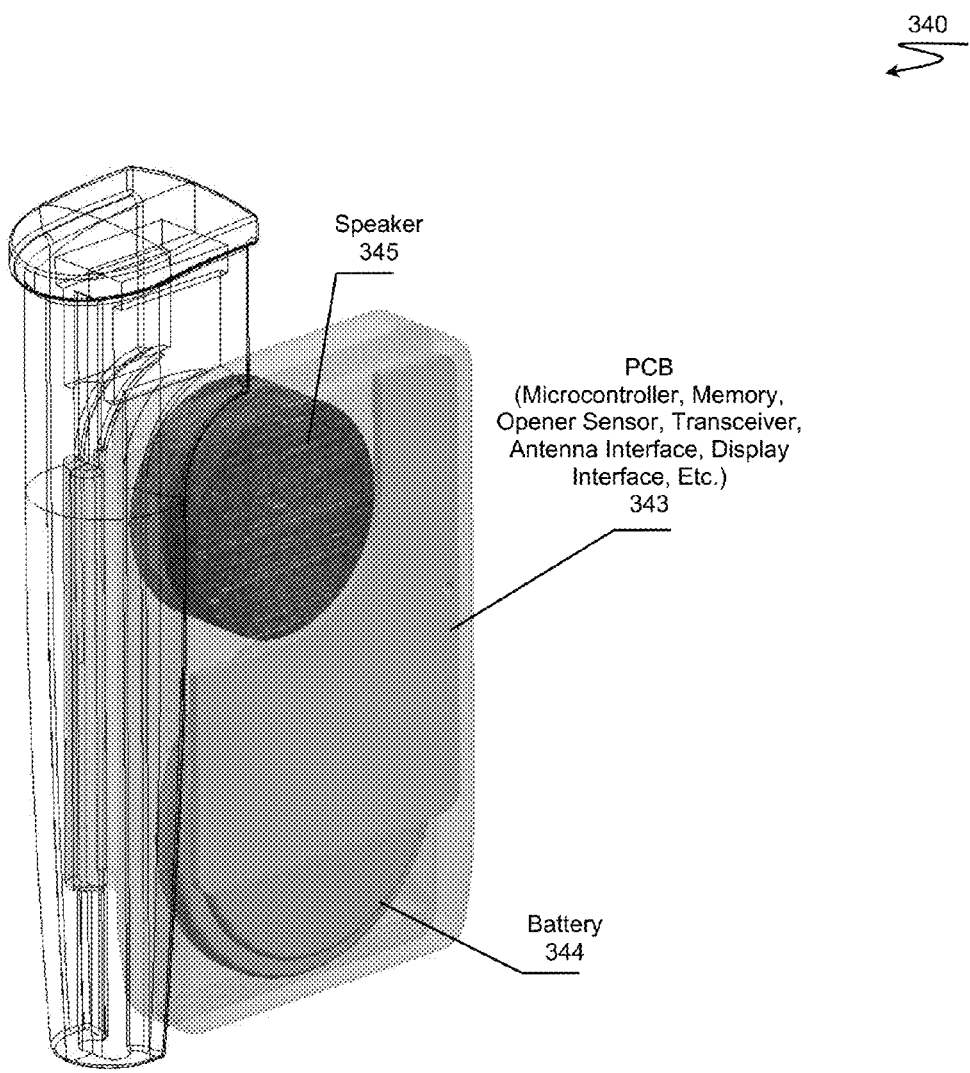
FIG. 3 presents a detailed isometric view of an electronic assembly.

FIG. 3 presents a more detailed view of a possible arrangement for an electronic assembly 340. Electronic assembly 340 is disposed within a bag and comprises sufficient elements to collect usage data and transmit data to an external data store. Electronic assembly 340 can include one or more of printed circuit board (PCB) 343, speaker 345, batter 344, or other components. For example PCB 343 can be populated with a microcontroller and memory coupled with other interfaces or communication elements. The memory (e.g., flash, ROM, RAM, SSD, memory card, micro hard disk, etc.) can store software instructions that configure the microcontroller to perform actions representative of the roles or responsibility of the bag as discussed herein. Additional components coupled with PCB 343 can include an opener sensor or sensor interface (e.g., Hall Effect sensor, RFID reader, etc.), transceivers or PHYs that enable wired or wireless communications, an antenna interface, a display interface capable of presenting information via a display (e.g., LEDs, LCDs, e-Ink, etc.), or other components. Such features are considered well within the ability of one skilled in the art.

FIG. 4 presents alternative bag 400 as an example of the breadth of possible applications of the inventive subject matter. For example, bag 400 can be sized and dimension according to different purposes. Bag 400 can be wider, thinner, longer, shorter, deeper, or have other dimensions. Further, bag 400 can be configured to fold over itself in a wallet-like fashion.

Of particular note, electronic assembly 440 is illustrated as being external to bag 400 where electronic assembly 440 is detachable from bag 440. In the example shown, electronic assembly 440 clips, or possibly locks, onto opener 420. In such an embodiment, the non-rigid rims or walls of bag 440 could include a passive trigger element (e.g., magnet) while electronic assembly 440 includes an opener sensor, which moves along with opener 420. Electronic assembly 440 can also comprise battery tray drawer 449 through which a user can replace batteries of electronic assembly 440.

In embodiments having a detachable electronic assembly 440, electronic assembly 440 can mate with one or more physical interfaces, possibly via a multi-pin cabled connector. Thus, a user can insert the electronic assembly 440 into a receptacle, possibly having a hard shell, and plug the assembly into the interface. The interfaces can then provide electronic access to sensors, displays, or other active components associated with the bag.

Bags can include see-through panels allowing a user to observe contents within the bag. In some embodiments, the see-through panels can comprise UV filtering materials to prevent light exposure to the contents. Contemplated bags can be made from multiple materials include injection molded parts, canvas, brushed aluminum, or other materials.

Many additional features can also be incorporated into the contemplated bags. Bags can be equipped with one or more environmental control features that ensure the contents remain within desirable environmental conditions. Bags can include humidity controls, temperature controls (e.g., heaters or coolers), gas filters, UV filters, or other environmental controls.

Contemplated bags are also robust against environment conditions. Preferred materials protect the electronic assembly from temperature extremes (e.g., freeze-thaw events, etc), punctures, shock, or other conditions. For example, bags could be made from Kevlar® or other robust materials, could have padding, or multiple seals.

In some embodiments, the electronic assembly can include a card reader. A consumer can swipe a card having an identification code to active or otherwise unlock the bag. The card reader can read the identification code (e.g., QR code, bar code, photograph of the user, RFID, magnetic strip, etc.) to determine if the consumer is authorized to access the contents.

Although the inventive subject matter is directed toward bags designed to hold pharmaceuticals, one should appreciate the techniques can be applied to broader markets. Example non-medical containers could include refrigerators, boxes, shopping bags, wallets, purses, pockets, backpacks, or other containers.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:
1. A sensor equipped bag comprising:
a main body having an opening and a cavity defined by one or more flexible walls;
a flexible seal assembly comprising non-rigid rims attached to an opening in the main body and configured to seal the cavity by joining the non-rigid rims;

an opener coupled with the seal assembly and capable of opening or closing the seal assembly by coupling or decoupling the non-rigid rim respectively;

a sensor that senses opener attributes associated with an opening actuation event, the opener attributes comprising grip pressure applied to the opener and rate at which the opener is moved, wherein the opening actuation event comprises an opening or closing of the bag; and an electronic assembly comprising an opener sensor circuit coupled to the sensor, wherein the opener sensor circuit processes the sensed opener attributes from the sensor and detects the opening actuation event.

2. The bag of claim 1, wherein the sensor comprises a piezoelectric sensor.

3. The bag of claim 1, wherein the opening actuation event is indicative of a use of contents inside the cavity of the bag.

4. The bag of claim 3, wherein the content comprises a plurality of doses of pharmaceuticals, wherein a number of the detected opening actuation events is indicative of an estimated number of doses used.

5. The bag of claim 3, wherein a duration of time between an opening of the bag and a successive closing of the bag is indicative of a use time of the contents.

6. The bag of claim 3, wherein the opening actuation event comprises a partial opening of the bag, wherein an extent of the partial opening is indicative of a type of the contents used.

7. The bag of claim 1, wherein the opener attributes indicate a mode of interaction between a user and the bag.

8. The bag of claim 1, wherein the electronic assembly is disposed within the bag.

9. The bag of claim 1, wherein the electronic assembly is disposed within the opener.

10. The bag of claim 1, further comprising an opener lock coupled with the electronic assembly locking the opener in a closed position, wherein the electronic assembly stores scheduling criteria for access to contents within the bag, wherein the electronic assembly disengages the opener lock based on the scheduling criteria, unlocking the opener.

11. The bag of claim 10, wherein the electronic assembly comprises a lock circuit that operates the opener lock.

12. The bag of claim 1, wherein the electronic assembly further comprises a transceiver capable of communicating with an external computer.

13. The bag of claim 12, wherein the electronic assembly is further configured to exchange the processed sensed opener attributes with the external computer.

14. The bag of claim 1, further comprising electronic indicators coupled with the electronic assembly, wherein the electronic assembly provides feedback via the electronic indicators.

15. The bag of claim 14, wherein the electronic indicators comprise a visual display and an audio port.

16. The bag of claim 15, wherein the visual display comprises at least one of the following: an e-ink display, a liquid crystal display, and a light emitting diode display.

17. The bag of claim 15, wherein the audio port comprises a speaker.

18. The bag of claim 14, wherein the electronic indicators comprise at least a tactile display.

19. The bag of claim 1, wherein the non-rigid rims comprise a mechanical seal.

20. The bag of claim 1, wherein the electronic assembly further comprises a communication activation trigger, wherein the electronic assembly transmits a message to a remote computing device upon actuation of the communication activation trigger.

* * * * *